United States Patent
Poydenot et al.

(10) Patent No.: US 11,382,872 B2
(45) Date of Patent: Jul. 12, 2022

(54) LSD1 INHIBITORS AS SKELETAL MUSCLE HYPERTROPHY INDUCERS

(71) Applicant: CYTOO, Grenoble (FR)

(72) Inventors: Pauline Poydenot, Saint Martin d'Heres (FR); Joris Michaud, Lausanne (CH); Mélanie Flaender, Grenoble (FR); Eve Duchemin-Pelletier, Vizille (FR); Luc Selig, Charenton le Pont (FR)

(73) Assignee: CYTOO, Grenoble (FR)

(*) Notice: Subject to any disclaimer, the term of this patent is extended or adjusted under 35 U.S.C. 154(b) by 119 days.

(21) Appl. No.: 16/461,076

(22) PCT Filed: Nov. 17, 2017

(86) PCT No.: PCT/EP2017/079674
§ 371 (c)(1),
(2) Date: May 15, 2019

(87) PCT Pub. No.: WO2018/091691
PCT Pub. Date: May 24, 2018

(65) Prior Publication Data
US 2020/0054578 A1    Feb. 20, 2020

(30) Foreign Application Priority Data

Nov. 17, 2016 (EP) .................................... 16306509

(51) Int. Cl.
| | | |
|---|---|---|
| *A61K 31/13* | (2006.01) | |
| *A61P 21/00* | (2006.01) | |
| *A61K 31/366* | (2006.01) | |
| *A61K 31/4409* | (2006.01) | |
| *A61K 31/4468* | (2006.01) | |
| *A61K 31/4965* | (2006.01) | |

(52) U.S. Cl.
CPC ............ *A61K 31/13* (2013.01); *A61K 31/366* (2013.01); *A61K 31/4409* (2013.01); *A61K 31/4468* (2013.01); *A61K 31/4965* (2013.01); *A61P 21/00* (2018.01)

(58) Field of Classification Search
CPC combination set(s) only.
See application file for complete search history.

(56) References Cited

U.S. PATENT DOCUMENTS

| 2012/0108648 A1 | 5/2012 | Nakao et al. | |
|---|---|---|---|
| 2012/0329800 A1* | 12/2012 | Bonaldo | A61K 31/137 514/237.8 |
| 2013/0231342 A1* | 9/2013 | Munoz | A61K 31/422 514/242 |

FOREIGN PATENT DOCUMENTS

| WO | WO 2010/116673 | 10/2010 |
|---|---|---|
| WO | WO 2012/024535 | 2/2012 |
| WO | WO 2013/019623 | 2/2013 |
| WO | WO 2015/061568 | 4/2015 |
| WO | WO 2016/043874 | 3/2016 |
| WO | WO 2018/091688 | 5/2018 |

OTHER PUBLICATIONS

Written Opinion in International Application No. PCT/EP2017/079674, dated Jan. 25, 2018, pp. 1-7.
Arora, R. C. et al. "Characterization of Rat Skeletal Muscle Monoamine Oxidase" *Biochemical Pharmacology*, 1977, pp. 45-49, vol. 26.
Choi, J. et al. "Histone demethylase LSD1 is required to induce skeletal muscle differentiation by regulating myogenic factors" *Biochemical and Biophysical Research Communications*, 2010, pp. 327-332, vol. 401.
Prusevich, P. et al. "A Selective Phenelzine Analogue Inhibitor of Histone Demethylase LSD1" *ACS Chem. Bio.*, Apr. 7, 2014, pp. 1284-1293, vol. 9.

* cited by examiner

*Primary Examiner* — Jeffrey S Lundgren
*Assistant Examiner* — Michael J Schmitt
(74) *Attorney, Agent, or Firm* — Saliwanchik, Lloyd & Eisenschenk

(57) ABSTRACT

The present invention relates to LSD1 inhibitors and their uses as skeletal muscle hypertrophy inducers as well as to promote skeletal muscle regeneration, to prevent skeletal muscle atrophy, or in the treatment or prevention of a disease or injury resulting in loss of skeletal muscle tissue and/or muscle weakness. It further relates to the non-therapeutic use of such compounds to increase muscle mass, muscle strength and/or muscle performance in a subject.

9 Claims, 1 Drawing Sheet

LSD1 INHIBITORS AS SKELETAL MUSCLE HYPERTROPHY INDUCERS

CROSS-REFERENCE TO RELATED APPLICATION

This application is the U.S. national stage application of International Patent Application No. PCT/EP2017/079674, filed on Nov. 17, 2017.

FIELD OF THE INVENTION

The present invention relates to therapeutic strategies to induce skeletal muscle hypertrophy, prevent atrophy or treat or prevent diseases or injuries resulting in loss of skeletal-muscle tissue and/or muscle weakness. It also relates to a non-therapeutic use of skeletal muscle hypertrophy inducers.

BACKGROUND OF THE INVENTION

Muscle wasting and weakness may result from a large panel of disease states and conditions including metabolic diseases, neurologic diseases, muscle diseases, acute or chronic illness (cachexia), aging, inactivity, food starvation and even poisoning. During the last 15 years, extensive research has led to a better understanding of the signalling pathways implicated in the loss of muscle mass. However, to date, the offer of therapeutic strategies directly targeting the muscle remains poor.

Muscle loss may occur, in particular, with aging and is a component of the frailty syndrome. Named "sarcopenia", this degenerative loss results in direct muscle atrophy and carries an increased risk for poor health outcomes including falls, incident disability, hospitalization, and mortality. With a growing older population, sarcopenia is an ever increasing global health concern and there has been great interest in developing approaches to counteract the effects of sarcopenia, and thereby reduce the age-related decline and disability. Potential interventions for sarcopenia may include physical activity and nutritional supplementation but, to date, pharmacological interventions have shown limited efficacy.

Muscle weakness can also directly result from neuromuscular disorders such as myopathies, neuromuscular junction diseases or motor neuron diseases.

Myopathies are neuromuscular disorders in which the primary symptom is muscle weakness due to dysfunction of skeletal muscle fibres. Myopathies can be inherited or acquired and include, for example, muscular dystrophies, metabolic myopathies such as mitochondrial myopathies or drug-induced myopathies, and autoimmune myopathies such as dermatomyositis, polymyositis or inclusion body myositis.

Among myopathies, muscular dystrophies represent a large group causing a progressive degeneration of myofibers and resulting in a loss of muscle mass. Mutations in over 30 genes causing muscular dystrophies have been identified. Duchenne Muscular Dystrophy (DMD) is the most common form of muscular dystrophy with an occurrence rate of about one in 3,500 males worldwide.

Treatments for neuromuscular disorders depend on the disease and specific causes, however, to date, there is no specific treatment to stop or reverse any form of muscular dystrophy. Exercise and nutritional interventions have merit for slowing the rate of muscle atrophy in some muscle wasting conditions, but in most cases they cannot halt the wasting process.

Therefore, there is a strong need for new therapeutic options that can efficiently attenuate muscle atrophy, promote muscle growth, increase muscle mass and ultimately improve the quality of life for patients.

SUMMARY OF THE INVENTION

The object of the present invention is to provide new therapeutic strategies to induce skeletal muscle hypertrophy, or prevent muscular atrophy, promote skeletal muscle regeneration, and treat or prevent skeletal muscle wasting.

In a first aspect, the invention relates to a LSD1 inhibitor for use as skeletal muscle hypertrophy inducer, for use to promote skeletal muscle regeneration and/or prevent skeletal muscle atrophy, or for use in the treatment or prevention of a disease or disorder resulting in loss of skeletal muscle tissue and/or muscle weakness.

Preferably, the LSD1 inhibitor is selected from the group consisting of small molecules inhibiting LSD1 demethylase activity, nucleic acid molecules interfering specifically with LSD1 expression, bait-substrates, and aptamers or antibodies directed against LSD1.

In particular, the LSD1 inhibitor may be a small molecule inhibiting LSD1 demethylase activity, preferably selected from the group consisting of cyclopropylamide-based LSD1 inhibitors, peptide-based inhibitors, phenelzine, polyamine analogues, isosteric ureas and thioureas, chemical inhibitors exhibiting a guanidinium group, namoline, SP2509 and pargyline. Alternatively, the LSD1 inhibitor may be selected from the group consisting of peptide-based inhibitors, phenelzine and its analogues, isosteric ureas and thioureas and namoline, preferably from phenelzine and its analogues, more preferably is bizine. Alternatively, the LSD1 inhibitor may be selected from the group consisting of cyclopropyl-amide-based LSD1 inhibitors, peptide-based inhibitors, phenelzine and its analogues, isosteric ureas and thioureas and namoline, preferably from the group consisting of cyclopropylamide-based LSD1 inhibitors and phenelzine and its analogues, preferably bizine.

More preferably, the LSD1 inhibitor is a cyclopropylamine-based LSD1 inhibitor, in particular a 2-phenylcyclopropan-1-amine or a derivative thereof.

In preferred embodiments, the LSD1 inhibitor is selected from the group consisting of

| Name | Formula |
|---|---|
| Tranylcypromine | |

-continued
| Name | Formula |
|---|---|
| RN-1 (hydrochloride) | 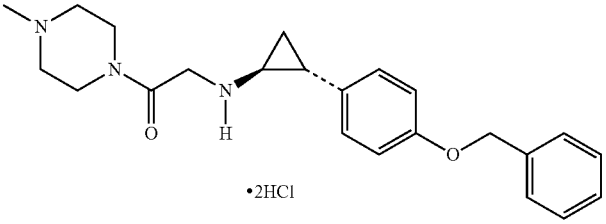 •2HCl |
| GSK LSD1 dihydrochloride | 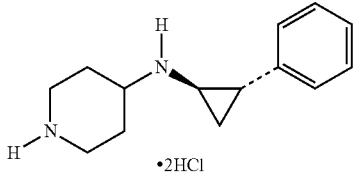 •2HCl |
| OG-L002 | 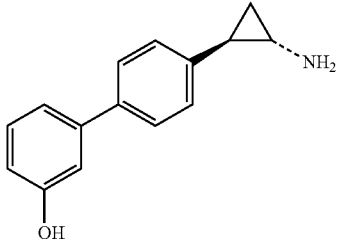 [SMILES: N[C@H]1C[C@@H]1c1ccc(-c2cccc(O)c2)cc1] |
| Trans-N-((2,3-dihydrobenzo[b](1,4]dioxin-6-yl)methyl)-2-phenylcyclopropan-1-amine | 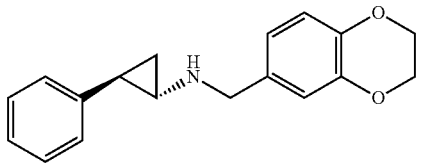 [SMILES: c1ccc([C@H]2C[C@@H]2NCc2ccc3c(c2)OCCO3)cc1] |
| Trans-N-((2-methoxypyridin-3-yl)methyl)-2-phenylcyclopropan-1-amine | 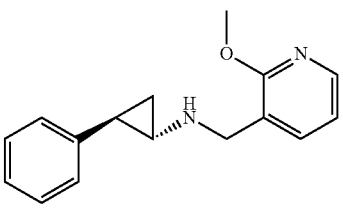 [SMILES: COc1ncccc1CN[C@H]1C[C@@H]1c1ccccc1] |
| ORY-1001 (CAS number: 1431326-61-2) | 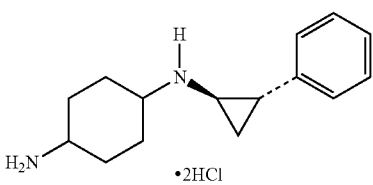 •2HCl |
| OG86 (also known as compound B) | 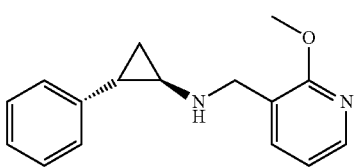 |

| Name | Formula |
|---|---|
| GSK2879552 (CAS number: 1401966-69-5) | 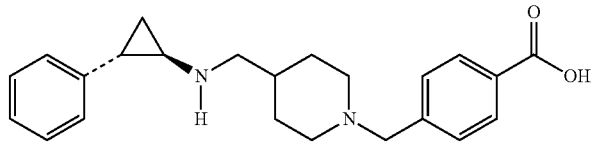 [SMILES: O=C(O)c1ccc(CN2CCC(CN[C@@H]3C[C@H]3c3ccccc3)CC2)cc1] |

ORY-2001 and compounds 1, 2, 3 and 4 as follow

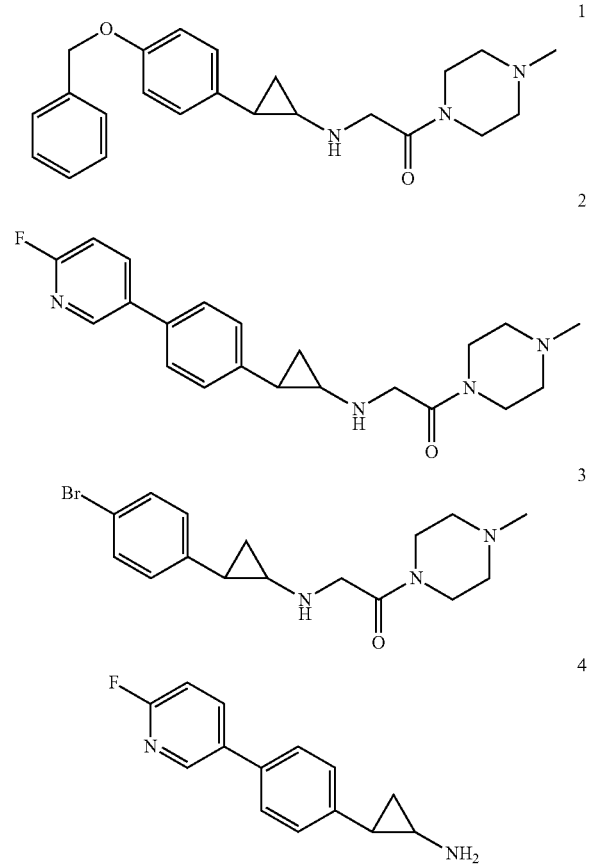

or any pharmaceutically acceptable salt, hydrate, solvate or prodrug thereof.

Preferably, the LSD1 inhibitor is selected from the group consisting of tranylcypromine, RN-1 (hydrochloride) and GSK LSD1, or any pharmaceutically acceptable salt, hydrate, solvate or prodrug thereof, more preferably is tranylcypromine, or any pharmaceutically acceptable salt, hydrate, solvate or prodrug thereof.

In some embodiments, the LSD1 inhibitor is a 2-phenyl-cyclopropan-1-amine derivative, or any pharmaceutically acceptable salt, hydrate, solvate or prodrug thereof, preferably selected from the group consisting of GSK LSD1 dihydrochloride, RN-1 (hydrochloride), OG-L002, Trans-N-((2,3-dihydrobenzo[b][1,4]dioxin-6-yl)methyl)-2-phenylcyclopropan-1-amine, Trans-N-((2-methoxypyridin-3-yl)methyl)-2-phenylcyclopropan-1-amine, ORY-1001, OG86, GSK2879552, ORY-2001 and compounds 1, 2, 3 and 4 as defined above, and any pharmaceutically acceptable salt, hydrate, solvate or prodrug thereof. More preferably, the LSD1 inhibitor is GSK LSD1 dihydrochloride, or any pharmaceutically acceptable salt, hydrate, solvate or prodrug thereof.

In particular embodiments, the LSD1 inhibitor is selected from the group consisting of cyclopropylamine-based LSD1 inhibitor and bizine, preferably from tranylcypromine, RN-1, GSK LSD1 and bizine, even more preferably from RN-1, GSK LSD1 and bizine, and any pharmaceutically acceptable salt, hydrate, solvate or prodrug thereof. Alternatively, the LSD1 inhibitor may be selected from the group consisting of 2-phenylcyclopropan-1-amine derivatives and bizine, preferably from the group consisting of bizine, GSK LSD1 dihydrochloride, RN-1 (hydrochloride), OG-L002, Trans-N-((2,3-dihydrobenzo [b](1,4]dioxin-6-yl)methyl)-2-phenylcyclopropan-1-amine, Trans-N-((2-methoxypyridin-3-yl)methyl)-2-phenylcyclopropan-1-amine, ORY-1001, OG86, GSK2879552, ORY-2001 and compounds 1, 2, 3 and 4 as defined above, and any pharmaceutically acceptable salt, hydrate, solvate or prodrug thereof.

In preferred embodiments, RN-1 is RN-1 hydrochloride and/or GSK LSD1 is GSK LSD1 dihydrochloride.

The disease or disorder resulting in loss of skeletal muscle tissue and/or muscle weakness, may be selected from sarcopenia, cachexia, neuromuscular diseases, muscle disuse atrophy, atrophy induced by anorexia food starvation, and muscle injuries including acute muscular injury or muscle overuse injury, preferably from sarcopenia, cachexia and neuromuscular diseases, in particular Duchenne muscular dystrophy, Becker muscular dystrophy, myotonic muscular dystrophies, distal muscular dystrophies such as Miyoshi muscular dystrophy, and limb-girdle muscular dystrophies, more preferably from sarcopenia and cachexia, and even more preferably sarcopenia.

In another aspect, the present invention also relates to a product containing a LSD1 inhibitor, and a compound inducing skeletal muscular atrophy, as a combined preparation for simultaneous, separate or sequential use.

Preferably, the compound inducing skeletal muscular atrophy is a therapeutic agent, more preferably selected from the group consisting of corticosteroids, colchicine, chloroquine, hydroxychloroquine, D-penicillamine, antibiotics, betablockers, amiodarone, cimetidine, zidovudine, vincristine, clofibrate, statins, fibrates, cyclosporine, L-tryptophan, drugs causing hypokalaemia, lipid lowering agents, and therapeutic agents administered by intramuscular route such as vaccines, and even more preferably is a lipid lowering agent, such as statins and fibrates.

In another aspect, the present invention also relates to a non-therapeutic use of a LSD1 inhibitor to increase muscle mass, muscle strength and/or muscle performance in a subject, and in particular to increase skeletal muscle mass, skeletal muscle strength and/or skeletal muscle performance in a subject.

The present invention also relates to a non-therapeutic use of a LSD1 inhibitor, to prevent loss of skeletal muscle mass in a subject, or as ingredient or additive for animal feed composition.

The present invention further relates to a method of improving livestock performance comprising providing to said livestock a LSD1 inhibitor, preferably a feed composition, ingredient, additive, or dietary supplement comprising a LSD1 inhibitor.

It also relates to the use, preferably the non-therapeutic use, of a LSD1 inhibitor as ingredient or additive for animal feed composition.

DETAILED DESCRIPTION OF THE INVENTION

Figure 1A:
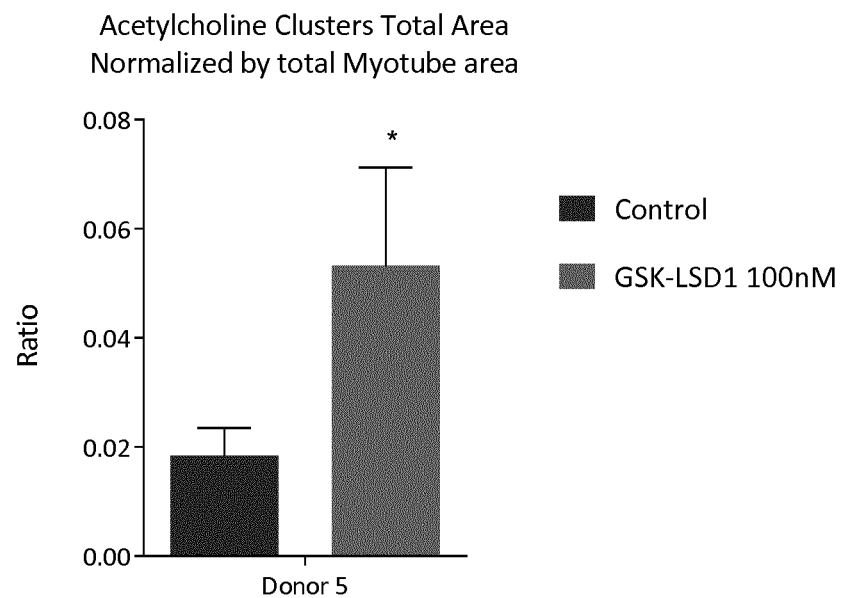
FIG. 1: Acetylcholine cluster total area normalized by total myotube area for donor 5 (A) and donor 3 (B).

Human lysine-specific demethylase 1A (LSD1), also known as lysine-specific histone demethylase 1A is an enzyme encoded by the KDM1A gene and belonging to the superfamily of the flavin adenine dinucleotide (FAD)-dependent amine oxidases. LSD1 specifically demethylates mono- or dimethylated histone H3 lysine4 (H3K4) and H3 lysine 9 (H3K9) via a redox process. LSD1 was shown to play an important role in a broad spectrum of biological processes, including cell proliferation, adipogenesis, spermatogenesis, chromosome segregation and embryonic development. Based on results obtained from C2C12 mouse myoblast cells, it was also found that LSD1 demethylates Myocyte Enhancer Factor 2 (MEF2), activates its transcriptional activity and thus stimulates skeletal muscle cell differentiation (Choi et al., Nucleic Acids Research, 2014, Vol. 42, No. 1).

Thanks to their solid knowledge on micropattern technology and a proprietary physiological human skeletal muscle model (MyoScreen™, CYTOO) allowing fully maturation of human primary myoblasts and providing myotubes with a high level of striation, high fusion index with aligned nuclei and low morphological variability, the inventors herein surprisingly demonstrated that, contrary to the teaching of this prior art, LSD1 inhibitors exhibit skeletal muscle hypertrophy activity and are not only able to increase myotube differentiation and size from myoblasts, but are also able to prevent muscular atrophy.

Accordingly, in a first aspect, the present invention relates to the use of a LSD1 inhibitor as skeletal muscle hypertrophy inducers, to promote skeletal muscle regeneration, to prevent skeletal muscle atrophy, or in the treatment or prevention of a disease or injury resulting in loss of skeletal muscle tissue and/or muscle weakness.

The present invention thus relates to a LSD1 inhibitor for use as skeletal muscle hypertrophy inducer.

As used herein, the term "LSD1 inhibitor" refers to a molecule which inhibits or reduces the activity of LSD1, i.e. inhibits or reduces the demethylase activity of LSD1, in particular on lysine 4 (H3K4me) and lysine 9 (H3K9me) of histone H3.

The demethylase activity of LSD1 can be easily assayed by any method known in the art. In particular, numerous assay kit are commercially available from various suppliers such as Cayman chemicals, Epigentec or Abcam. LSD1 enzyme inhibition may be carried out using any known method such as the inhibition assay published by Feng et al. (Feng et al. Journal of Hematology & Oncology (2016) 9:24) or Wang et al. (Wang et al. Cancer Res. 2011 71(23): 7238-7249).

The LSD1 inhibitor may covalently or non-covalently bind to LSD1 or FAD and thus modifying the activity by steric hindrance or modification. This inhibitor can be, for instance, a small molecule, a substrate-like peptide inhibitor (i.e. a bait-substrate), an aptamer or an antibody directed against LSD1. The inhibition can also be due to a reduction or suppression of the KDM1A gene expression, for example by using specific RNAi, antisense or ribozyme.

Preferably, the LSD1 inhibitor is selected from the group consisting of small molecules inhibiting LSD1 demethylase activity, nucleic acid molecules interfering specifically with LSD1 expression, bait-substrates, and aptamers or antibodies directed against LSD1. More preferably, the LSD1 inhibitor is selected from the group consisting of small molecules inhibiting LSD1 demethylase activity, nucleic acid molecules interfering specifically with LSD1 expression and bait-substrates. Even more preferably, the LSD1 inhibitor is selected from the group consisting of small molecules inhibiting LSD1 demethylase activity and nucleic acid molecules interfering specifically with LSD1 expression.

In an embodiment, the LSD1 inhibitor is a nucleic acid molecule interfering specifically with LSD1 expression.

As used herein, the term "nucleic acid molecule" includes, but is not limited to, RNAi, antisense and ribozyme molecules. In the present invention, a "nucleic acid molecule interfering specifically with LSD1 expression" is a nucleic acid molecule which is able to reduce or to suppress the expression of the KDM1A gene, in a specific way. As used herein, the term "RNAi" refers to any RNA which is capable of down-regulating the expression of the targeted protein. It encompasses small interfering RNA (siRNA), double-stranded RNA (dsRNA), single-stranded RNA (ssRNA), micro-RNA (miRNA), and short hairpin RNA (shRNA) molecules. Methods of designing, producing and using such interfering nucleic acid molecule are well known by the skilled person.

Examples of such interfering nucleic acid molecules include, but are not limited to, shRNAs targeting LSD1 described in Fiskus et al. Leukemia. 2014 November; 28(11): 2155-2164, miRNA 137 repressing LSD1 expression by targeting its 3' UTR described in Sun et al. Nature Communications 2011; or a siRNA targeting LSD1 described in Kong et al. Oncology Letters. 2016; 11:2475-2480.

In another embodiment, the LSD1 inhibitor is a bait-substrate.

As used herein, the term "bait-substrate" designates a substrate-like peptide inhibitor, i.e. a peptide which is able to bind to LSD1 and thus prevent interaction of LSD1 with its substrate, in particular with histone H3.

Examples of such bait-substrates include, but are not limited to, a bait-substrate derived from the N-terminal 21 amino-acid residues of histone H3 peptide in which lysine 4 is replaced by methionine. This bait binds to LSD1 with high binding affinity and acts as an inhibitor (Wang et al., 2011, supra). Another series of candidates for the histone H3 peptide based LSD1-selective inhibitor were designed and tested, leading to the identification of a peptide which has a phenylcyclopropylamine (PCPA) moiety at Lys-4 of the 21 amino acid residues of histone H3 (T. Kakizawa et al. Bioorg. Med. Chem. Lett. 25 (2015) 1925-1928).

In another embodiment, the LSD1 inhibitor is an antibody directed against LSD1.

In another embodiment, the LSD1 inhibitor is an antibody directed against LSD1

The term "antibody" herein is used in the broadest sense and specifically covers monoclonal antibodies, polyclonal antibodies, antibody fragments, and derivatives thereof, so long as they specifically bind to the molecular target of interest. As used herein, the term "antibody fragment" refers to a protein comprising a portion of a full length antibody, generally the antigen binding or variable domain thereof. Examples of antibody fragments include Fab, Fab', F(ab)$_2$, F(ab')$_2$, F(ab)$_3$, Fv (typically the VL and VH domains of a single arm of an antibody), single-chain Fv (ScFv), dsFv, Fd (typically the VH and CH1 domains) and dAb (typically a VH domain) fragments, nanobodies, minibodies, diabodies, triabodies, tetrabodies, kappa bodies, linear antibodies, and other antibody fragments that retain antigen-binding function (e.g. Holliger and Hudson, Nat Biotechnol. 2005 September; 23(9):1126-36). Antibody fragments can be made by various techniques, including but not limited to proteolytic digestion of intact antibody as well as recombinant host cells (e.g. E. coli or phage). These techniques are well-known by the skilled person and are extensively described in the literature. The term "antibody derivative", as used herein, refers to an antibody provided herein, e.g. a full-length antibody or a fragment of an antibody, wherein one or more of the amino acids are chemically modified, e.g. by alkylation, PEGylation, acylation, ester or amide formation or the like. In particular, this term may refer to an antibody provided herein that is further modified to contain additional nonproteinaceous moieties that are known in the art and readily available.

In another embodiment, the LSD1 inhibitor is an aptamer directed against LSD1. The aptamer may be a peptide aptamer or a nucleic acid aptamer.

Peptides aptamers consist of a short variable peptide loop attached at both ends to a protein scaffold such as the bacterial protein thioredoxin-A. Typically, the variable loop length is composed of ten to twenty amino acids. Peptide aptamer specific of a target of interest may be selected using any method known by the skilled person such as the yeast two-hybrid system or Phage Display. Peptides aptamers may be produced by any method known by the skilled person such as chemical synthesis or production in a recombinant bacterium followed by purification.

Nucleic acid aptamers are a class of small nucleic acid ligands that are composed of RNA or single-stranded DNA oligonucleotides and have high specificity and affinity for their targets. Systematic Evolution of Ligands by EXponential enrichment (SELEX) technology to develop nucleic acid aptamers specific of a target of interest, is well known by the skilled person and may be used to obtain aptamers specific of a particular molecular target. Nucleic acid aptamers may be produced by any method known by the skilled person such as chemical synthesis or in vitro transcription for RNA aptamers. Nucleic acid aptamers may be selected from the group consisting of DNA aptamers, RNA aptamers, XNA aptamers (nucleic acid aptamer comprising xeno nucleotides) and spiegelmers (which are composed entirely of an unnatural L-ribonucleic acid backbone).

In a preferred embodiment, the LSD1 inhibitor is a small molecule inhibiting LSD1 demethylase activity.

As used herein, the term "small molecule inhibiting LSD1 demethylase activity" refers to small molecule that can be an organic or inorganic compound, usually less than 1000 daltons, with the ability to inhibit or reduce the activity of LSD1. This small molecule can be derived from any known organism (including, but not limited to, animals, plants, bacteria, fungi and viruses) or from a library of synthetic molecules.

The small molecule may be selected from the group consisting of cyclopropylamide-based LSD1 inhibitors, peptide-based inhibitors such as described by Culhane et al. (J Am Chem Soc. 2006 Apr. 12; 128(14):4536-7, and J. Am. Chem. Soc., 2010, 132 (9), pp 3164-3176), phenelzine and its analogues (Culhane et al., J. Am. Chem. Soc., 2010, 132 (9), pp 3164-3176, Prusevich et al. ACS Chem. Biol., 2014, 9 (6), pp 1284-1293), polyamine analogues such as the polyamine analogue 2d (1,15-bis {N(5)-[3,3-(diphenyl)propyl]-N(1)-biguanido}-4,12-diazapentadecane) and polyamine analogues described by Huang et al. (Proc Natl Acad Sci USA. 2007 May 8; 104(19):8023-8, and Clin Cancer Res. 2009 Dec. 1; 15(23):7217-28), isosteric ureas and thioureas such as described by Sharma et al. (J. Med. Chem., 2010, 53 (14), pp 5197-5212), chemical inhibitors exhibiting a guanidinium group which mimics arginines and form strong hydrogen bonds with the negatively charged residues of LSD1 (Wang et al., 2011, supra; in particular CBB1002, CBB1003, CBB1004, CBB1005, CBB1006, CBB1007 and CBB1008), namoline (Willmann et al., Int J Cancer. 2012 Dec. 1; 131(11):2704-9; Schmitt et al. J. Med. Chem. 2013, 56(18), 7334-7342), SP2509 (CAS number: 1423715-09-6, Sankar et al. Clin. Cancer Res. 20(17), 4584-4597 (2014) and Fiskus et al. Leukemia 28(11), 2155-2164 (2014)) and pargyline (CAS number: 555-57-7, Wand et al. Biochemical and Biophysical Research Communications (2015)).

In particular, the LSD1 inhibitor may be selected from the group consisting of cyclopropylamide-based LSD1 inhibitors, peptide-based inhibitors, phenelzine and its analogues, preferably bizine (CAS number: 1591932-50-1), isosteric ureas and thioureas. More particularly, the LSD1 inhibitor may be selected from the group consisting of cyclopropylamide-based LSD1 inhibitors and phenelzine and its analogues, preferably from the group consisting of cyclopropylamide-based LSD1 inhibitors and bizine.

Preferably, the small molecule is a cyclopropylamine-based LSD1 inhibitor, in particular selected from 2-phenylcyclopropan-1-amine and derivatives thereof, and substituted trans-2-arylcyclopropylamines such as described by Gooden et al (Bioorg Med Chem Lett 2008; 18:3047-51).

In a particular embodiment, the LSD1 inhibitor is a small molecule selected from 2-phenylcyclopropan-1-amine and derivatives thereof, preferably selected from trans-2-phenylcyclopropan-1-amine (tranylcypromine) and derivatives thereof.

In a preferred embodiment, the LSD1 inhibitor is a small molecule selected from

| Name | Formula |
|---|---|
| Tranylcypromine | 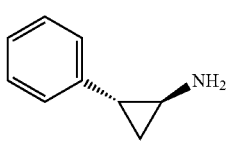 |

-continued

| Name | Formula |
|---|---|
| RN-1 (hydrochloride)<br>(CAS number: 1781835-13-9) | 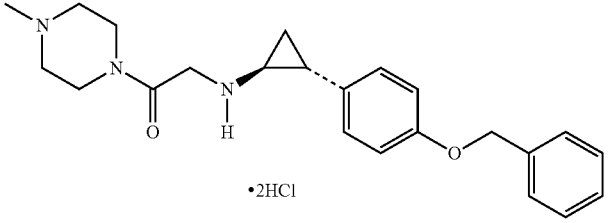<br>•2HCl |
| GSK LSD1 dihydrochloride<br>(CAS number: 1431368-48-7) | 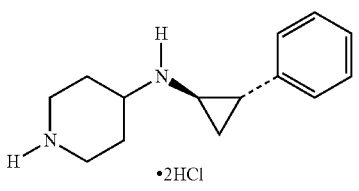<br>•2HCl |
| OG-L002<br>(CAS number: 1357302-64-7) | 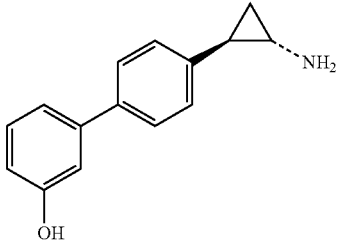 [SMILES: N[C@H]1C[C@@H]1c1ccc(-c2cccc(O)c2)cc1] |
| Trans-N-((2,3-dihydrobenzo[b]<br>(1,4]dioxin-6-yl)methyl)-2-<br>phenylcyclopropan-1-amine<br>(Lynch et al. Expert Opin. Ther.<br>Targets (2012) 16(12):1239-1249) | 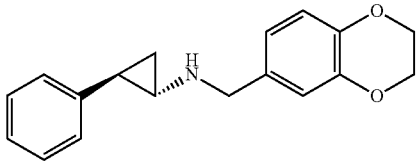 [SMILES: c1ccc([C@H]2C[C@@H]2NCc2ccc3c(c2)OCCO3)cc1] |
| Trans-N-((2-methoxypyridin-3-<br>yl)methyl)-<br>2-phenylcyclopropan-1-amine<br>(Lynch et al. Expert Opin. Ther.<br>Targets (2012) 16(12):1239-1249) | 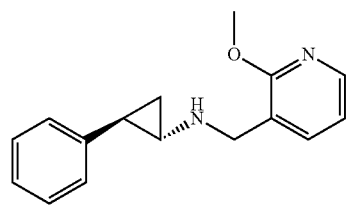 [SMILES: COc1ncccc1CN[C@H]1C[C@@H]1c1ccccc1] |
| ORY-1001<br>(CAS number: 1431326-61-2) | 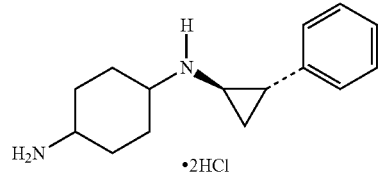<br>•2HCl |
| OG86<br>(also known as compound B) | 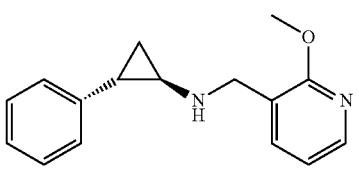 |

| Name | Formula |
|---|---|
| GSK2879552 (CAS number: 1401966-69-5) | 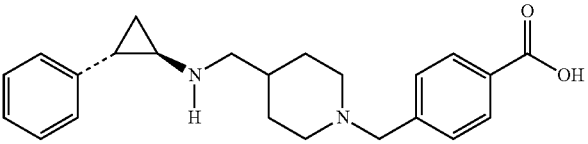 [SMILES: O=C(O)c1ccc(CN2CCC(CN[C@@H]3C[C@H]3c3ccccc3)CC2)cc1] |

ORY-2001 (Oryzon Genomics) and compounds 1, 2, 3 and 4 described in Feng et al., 2016 (supra):

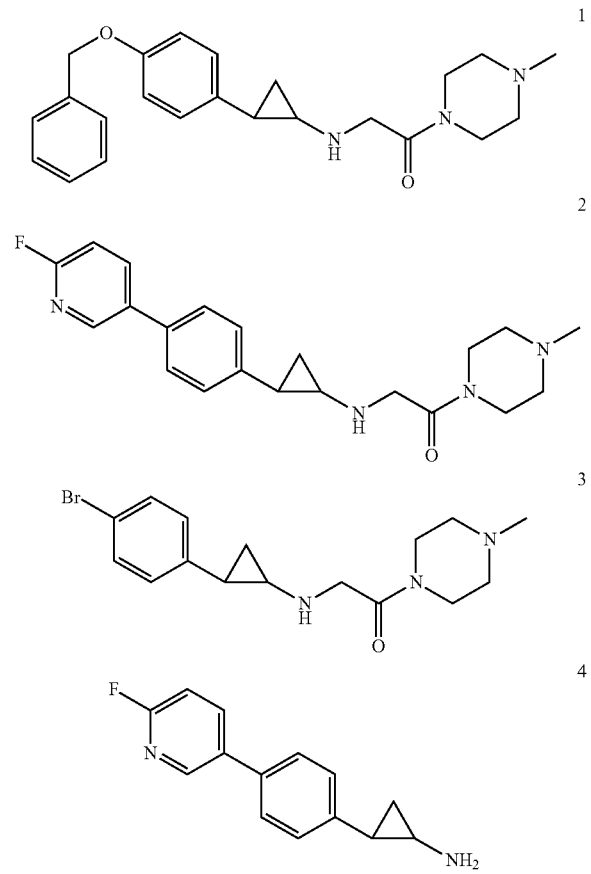

or any pharmaceutically acceptable salt, hydrate, solvate or prodrug thereof.

In a particular embodiment, the LSD1 inhibitor is selected from the group consisting of tranylcypromine, RN-1, preferably hydrochloride, and GSK LSD1, or any pharmaceutically acceptable salt, hydrate, solvate or prodrug thereof. In a more particular embodiment, the LSD1 inhibitor is tranylcypromine, or any pharmaceutically acceptable salt, hydrate, solvate or prodrug thereof.

In another particular embodiment, the LSD1 inhibitor is a cyclopropylamine-based LSD1 inhibitor is a cyclopropylamine-based LSD1 inhibitor but is not tranylcypromine. Preferably, the LSD1 inhibitor is a 2-phenylcyclopropan-1-amine derivative.

In particular, the LSD1 inhibitor may be selected from RN-1, preferably hydrochloride, GSK LSD1, OG-L002, Trans-N-((2,3-dihydrobenzo[b](1,4]dioxin-6-yl)methyl)-2-phenylcyclopropan-1-amine, Trans-N4(2-methoxypyridin-3-yl)methyl)-2-phenylcyclopropan-1-amine, ORY-1001, OG86, GSK2879552, ORY-2001 and compounds 1, 2, 3 and 4 described in Feng et al., 2016 (supra). Preferably, the LSD1 inhibitor is GSK LSD1 or any pharmaceutically acceptable salt, hydrate, solvate or prodrug thereof. In preferred embodiments, GSK LSD1 is GSK LSD1 dihydrochloride.

The LSD1 inhibitors may be used in the form of pharmaceutically acceptable salts, hydrates and solvates.

Said pharmaceutically acceptable salts, hydrates and solvates may be formed, where appropriate, by methods well known to those of skill in the art.

The term "pharmaceutically acceptable salt" refers to salts which are non-toxic for a patient and suitable for maintaining the stability of a therapeutic agent and allowing the delivery of said agent to target cells or tissue. Pharmaceutically acceptable salts are well known in the art.

As used herein, the term "solvate" refers to a solvent addition form that contains either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate. When the solvent is alcohol, the solvate formed is an alcoholate. Hydrates are formed by the combination of one or more molecules of water with one of the substances in which the water retains its molecular state as $H_2O$, such combination being able to form one or more hydrates.

The LSD1 inhibitors may also be used in the form of a prodrug. Prodrugs are generally drug precursors that, following administration to an individual and subsequent absorption, are converted to an active, or a more active species via some process, such as conversion by a metabolic pathway. Some prodrugs have a chemical group present on the prodrug that, for example, renders it less active, increases its solubility and/or improves safety profiles over administration of the parent drugs. In some instances, the prodrugs may be less susceptible to in vivo degradation and exhibit a greater half-life than its parent drug. Once the chemical group has been cleaved and/or modified from the prodrug, the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered and subsequently subjected to a biotransformation in vivo and thus provides a therapeutically effective concentration of an active agent. For further general examples, see: Bundgaard, "Design and Application of Prodrugs" in A Textbook of Drug Design and Development, Krosgaard-Larsen and Bundgaard, Ed., 1991, Chapter 5, 113-191, which is incorporated herein by reference. Prodrugs may be prepared, for example, by modifying functional groups present in the compound in such a way that the modifications are cleaved, either in routine manipulation or in vivo, to the parent compound.

The present invention also relates to a pharmaceutical composition comprising a LSD1 inhibitor and a pharmaceutically acceptable carrier and/or excipient, preferably for use as skeletal muscle hypertrophy inducer.

All embodiments described above for the LSD1 inhibitors as skeletal muscle hypertrophy inducers are also encompassed in this aspect.

The pharmaceutical composition of the invention is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

Possible pharmaceutical compositions include those suitable for oral, transmucosal (including nasal, rectal or vaginal), topical (including transdermal, buccal and sublingual), or parenteral (including subcutaneous, intramuscular, intravenous and intradermal) administration. For these formulations, conventional excipient can be used according to techniques well known by those skilled in the art. Preferably, the pharmaceutical composition of the invention is suitable for oral administration.

The compositions for parenteral administration are generally physiologically compatible sterile solutions or suspensions which can optionally be prepared immediately before use from solid or lyophilized form. Adjuvants such as a local anesthetic, preservative and buffering agents can be dissolved in the vehicle and a surfactant or wetting agent can be included in the composition to facilitate uniform distribution of the active ingredient.

For oral administration, the composition can be formulated into conventional oral dosage forms such as tablets, capsules, powders, granules and liquid preparations such as syrups, elixirs, and concentrated drops. Non toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical composition according to the invention may be formulated to release the active drug substantially immediately upon administration or at any predetermined time or time period after administration.

Pharmaceutical composition according to the invention can comprise one or more LSD1 inhibitors associated with one or several pharmaceutically acceptable excipients and/or carriers. These excipients and/or carriers are chosen according to the form of administration as described above.

Pharmaceutical composition according to the invention may also comprise one or several additional active compounds. Said additional active compounds may be selected, for example, from the group consisting of anti-inflammatories, protein anabolic agents (e.g. growth hormone or insulin-like growth factor I), antineoplastic agents, antibiotics, local anesthetics, anabolic/androgenic steroids (e.g. testosterone), glucocorticoids, appetite stimulants (e.g. dronabinol), cytokine modulators (e.g. thalidomide), angiotensin and beta-adrenoreceptor inhibitors, NHE-1 inhibitors (e.g. rimeporide), antifibrotic drugs (e.g. losartan or Lisinopril), phosphodiesterase 5 (PDE5) inhibitors (e.g. tadalafil or sildenafil), dehydroepiandrosterone, Vitamin D, ursolic acid, omega 3 acids, angiotensin-converting enzyme (ACE) inhibitors, proteasome inhibitors, cyclophilin D inhibitors, PGC-1 a (alpha) pathway modulators, myostatin and activin A antagonists, ghrelin agonists, β2-adrenoreceptor agonists, creatine supplements, antifibrotic drugs such as losartan and lisinopril, muscle ischemia therapies such as tadalafil and sildenafil, mutation specific therapies such as exon skipping therapies (e.g. eteplirsen, a morpholino phosphorodiamidate antisense oligomer targeting mutations implicated in DMD cases), and agents for therapeutic nonsense suppression such as ataluren, utrophin upregulators such as SMT-C1100.

In the experimental section, the inventors demonstrated that LSD1 inhibitors are able to promote the differentiation of myoblasts into myotubes, to increase the number and size of myotubes, and/or to increase the fusion index reflecting the capacity of cells to regenerate.

Accordingly, the present invention relates to a LSD1 inhibitor or a pharmaceutical composition according to the invention, for use as skeletal muscle hypertrophy inducer.

Skeletal muscle fibers are syncytia that arise from the sequential fusion of myoblast cells. The process involves i) the differentiation of myoblasts into myocytes, ii) the fusion of myocytes to form nascent myotubes and iii) additional fusion of myocytes with nascent myotubes to form more mature myotubes. Accordingly, as used herein, the expression «skeletal muscle hypertrophy» refers to a gain of skeletal muscle mass characterized by an increase in the size of pre-existing myofibers and/or an increase in the number of myofibers and/or an increase in the mean number of nuclei per myotube and/or an increase in the fusion index (number of nuclei in myotubes divided by total number of nuclei in myoblasts and myotubes). Preferably, the expression «skeletal muscle hypertrophy» refers by an increase in the size of pre-existing myofibers and/or an increase in the number of myofibers and/or an increase in the fusion index. As used herein, the terms "myotube" and "myofiber" are used interchangeably.

The present invention also relates to a method for inducing skeletal muscle hypertrophy in a subject in need thereof, comprising administering a therapeutically effective amount of a LSD1 inhibitor or a pharmaceutical composition according to the invention, to said subject.

The therapeutically effective amount to be administered may be easily chosen by the skilled person and should be sufficient to provide an increase of skeletal muscle mass or skeletal muscle strength in the subject.

As used herein, the subject is an animal, preferably a mammal, more preferably a human being. Preferably, the subject is a subject suffering from muscle wasting or weakness resulting from a disease or disorder resulting in loss of skeletal muscle tissue and/or skeletal muscle weakness, such as diseases or disorders described below.

The present invention further concerns the use of a LSD1 inhibitor or a pharmaceutical composition according to the invention for preparing a medicament inducing skeletal muscle hypertrophy.

The present invention also relates to a LSD1 inhibitor or a pharmaceutical composition according to the invention, for use to prevent involuntary loss of skeletal muscle mass, preferably due to the degeneration of muscle fibers, for use to promote or stimulate skeletal muscle mass increase, for use to replete skeletal muscle mass and/or for use to increase skeletal muscle mass and/or strength.

The present invention also relates to a method for preventing involuntary loss of skeletal muscle mass, preferably due to the degeneration of muscle fibers, promoting or stimulating skeletal muscle mass increase, repleting skeletal muscle mass and/or increasing skeletal muscle mass and/or strength, in a subject in need thereof, comprising administering a therapeutically effective amount of a LSD1 inhibitor or a pharmaceutical composition according to the invention, to said subject.

The therapeutically effective amount to be administered may be easily chosen by the skilled person and should be sufficient to prevent involuntary loss of skeletal muscle mass, to promote or stimulate skeletal muscle mass increase, to replete skeletal muscle mass and/or to increase skeletal muscle mass and/or strength.

The subject may be as defined above.

The present invention further concerns the use of a LSD1 inhibitor or a pharmaceutical composition according to the invention, for preparing a medicament preventing involuntary loss of skeletal muscle mass, preferably due to the degeneration of muscle fibers, promoting or stimulating skeletal muscle mass increase, repleting skeletal muscle mass and/or increasing skeletal muscle mass and/or strength.

In the experimental section, the inventors demonstrated that LSD1 inhibitors are not only able to promote the differentiation of myoblasts into myotubes and to increase the fusion index reflecting the capacity of cells to regenerate, but are also able to prevent skeletal muscle atrophy, in particular atrophy induced by IL-1β, TNF-α, myostatin, TGF-β and dexamethasone.

Thus, the present invention also relates to a LSD1 inhibitor or a pharmaceutical composition according to the invention, for use to promote skeletal muscle regeneration and/or prevent skeletal muscle atrophy.

All embodiments described above for the LSD1 inhibitors as skeletal muscle hypertrophy inducers are also encompassed in this aspect.

As used herein, the expression "skeletal muscle regeneration" refers to the capacity of muscle cells or tissue to regenerate, i.e. to produce new myotubes from myoblasts. The expression "to promote skeletal muscle regeneration" thus refers to the capacity of LSD1 inhibitors to promote differentiation of myoblasts into myotubes and/or to increase the number of myotubes and/or to improve the regeneration capacity of muscle tissue and in particular of myotubes.

As used herein, the expression "to prevent skeletal muscle atrophy" refers to the capacity of LSD1 inhibitors to prevent, stop or slow down muscle wasting. Muscle atrophy may be caused for example by a disease state, a particular physiological condition such as aging, food starvation or inactivity, or an atrophying agent such as drug (statins) or poison (botulinum toxin). Prevention of muscle atrophy is preferably obtained by increasing the production of muscle mass and then counter balancing muscle loss.

The present invention also relates to a method for promoting skeletal muscle regeneration and/or preventing skeletal muscle atrophy in a subject in need thereof, comprising administering a therapeutically effective amount of a LSD1 inhibitor or a pharmaceutical composition according to the invention, to said subject.

The therapeutically effective amount to be administered may be easily chosen by the skilled person and should be sufficient to stimulate skeletal muscle regeneration and/or prevent, stop or slow down muscle wasting, preferably by increasing the production of muscle mass and then counter balancing muscle loss.

The subject may be as defined above.

The present invention further relates to the use of a LSD1 inhibitor or a pharmaceutical composition according to the invention for preparing a medicament for promoting skeletal muscle regeneration and/or preventing skeletal muscle atrophy.

The present invention further relates to a LSD1 inhibitor or a pharmaceutical composition according to the invention for use in the treatment or prevention of muscle wasting, and in particular in the treatment or prevention of a disease or disorder resulting in loss of skeletal muscle tissue and/or skeletal muscle weakness.

It also concerns the use of a LSD1 inhibitor or a pharmaceutical composition according to the invention for preparing a medicament for treating muscle wasting, and in particular a disease or disorder resulting in loss of skeletal muscle tissue and/or skeletal muscle weakness.

It finally concerns a method for treating muscle wasting, and in particular a disease or disorder resulting in loss of skeletal muscle tissue and/or skeletal muscle weakness, in a subject in need thereof, comprising administering a therapeutically active amount of a LSD1 inhibitor or a pharmaceutical composition according to the invention to the subject.

All embodiments described above for the LSD1 inhibitors as skeletal muscle hypertrophy inducers are also encompassed in this aspect.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

As used herein, the term "treatment of muscle wasting" may refer to the therapy, prevention or retardation of involuntary loss of skeletal muscle mass, preferably due to the degeneration of muscle fibers.

In particular, the term "treatment of a disease or disorder resulting in loss of skeletal muscle tissue and/or skeletal muscle weakness" may refer to a preservation or increase of the skeletal muscle mass and/or the skeletal muscle strength of a patient or a slow-down of the skeletal muscle mass loss and/or the skeletal muscle strength loss of a patient.

The effective amount may be a therapeutically or prophylactically effective amount. A "therapeutically effective amount" refers to an amount effective, at dosages and for periods of time necessary, to achieve the desired therapeutic or prophylactic result. The therapeutically effective amount may vary according to factors such as the disease or disorder, disease state, age, sex, and weight of the individual. A therapeutically effective amount encompasses an amount in which any toxic or detrimental effects are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

The disease or disorder to be treated may be any disease or disorder resulting in loss of skeletal muscle tissue or mass and/or skeletal muscle weakness.

Muscle wasting (i.e. loss of skeletal muscle tissue) and weakness may result from a large panel of diseases or disorders such as metabolic diseases (e.g. glycogen storage diseases, lipid storage diseases or disorders of purine nucleotide metabolism), neurologic diseases (e.g. Hereditary Sensory and Motor Neuropathies type III) and neuromuscular diseases, cachexia (i.e. muscle atrophy resulting from diseases such as cancer, AIDS, congestive heart failure, chronic obstructive pulmonary disease, severe burns, renal failure or liver failure), sarcopenia, muscle disuse atrophy (i.e. atrophy caused by prolonged inactivity), atrophy induced by excessive food starvation such as starvation due to anorexia nervosa, or muscle injuries including acute muscular injury, muscle overuse injury, or wound war injuries.

Preferably, the disease or disorder to be treated is selected from neuromuscular diseases, cachexia, sarcopenia, muscle disuse atrophy, atrophy induced by anorexia food starvation, and muscle injuries including acute muscular injury or muscle overuse injury. More preferably, the disease or disorder to be treated is selected from neuromuscular diseases, cachexia and sarcopenia.

In a particular embodiment, the disease or disorder is a neuromuscular disease, preferably selected from muscle diseases (i.e. myopathies), neuromuscular junction diseases or motor neuron diseases.

Myopathies are neuromuscular disorders in which the primary symptom is muscle weakness due to dysfunction of skeletal muscle fibres. Myopathies can be inherited or acquired and include, for example, muscular dystrophies, metabolic myopathies such as mitochondrial myopathies or drug-induced myopathies, and autoimmune myopathies such as dermatomyositis, polymyositis or inclusion body myositis.

Muscular dystrophies represent a large group of myopathies causing a progressive degeneration of myofibers and resulting in a loss of muscle mass. Mutations in over 30 genes causing muscular dystrophies have been identified. Examples of muscular dystrophies include, but are not limited to Duchenne muscular dystrophy, Becker muscular dystrophy, congenital muscular dystrophies, facioscapulohumeral muscular dystrophies, myotonic muscular dystrophies, distal muscular dystrophies such as Miyoshi muscular dystrophy, Emery—Dreifuss muscular dystrophy, limb-girdle muscular dystrophies and oculopharyngeal muscular dystrophies.

Motor neuron diseases are disorders which are characterized by the gradual degeneration and death of motor neurons which control voluntary muscles. Motor neurons thus stop sending messages to muscles which gradually weaken and atrophy. Motor neuron diseases include, for example, amyotrophic lateral sclerosis, primary lateral sclerosis, progressive muscular atrophy, progressive bulbar palsy, pseudobulbar palsy and spinal muscular atrophies.

Neuromuscular junction diseases are disorders which have in common the perturbation of the neurotransmission through the neuromuscular junction and result in progressive weakness due to a reduced muscle strength. Neuromuscular junction diseases include, for example, myasthenia gravis, autoimmune neuromyotonia (Isaacs' syndrome), LambertEaton myasthenic syndrome, or may result of a form of poison that effects neuromuscular junction functioning such as snake venom or neurotoxins (e.g. *Clostridium botulinum* toxin).

Preferably, the neuromuscular disease is selected from muscular dystrophies, and in particular from Duchenne muscular dystrophy, Becker muscular dystrophy, myotonic muscular dystrophies, distal muscular dystrophies such as Miyoshi muscular dystrophy, and limb-girdle muscular dystrophies.

In another particular embodiment, the disease or disorder is selected from cachexia and sarcopenia, preferably is sarcopenia.

In the methods of the present invention, the LSD1 inhibitor or a pharmaceutical composition according to the invention may be used in combination with other active ingredients that can be chosen according to the disease to be prevented or treated. Examples of other active ingredients include, but are not limited to, anti-inflammatories, protein anabolic agents (e.g. growth hormone or insulin-like growth factor I), antineoplastic agents, antibiotics, local anesthetics, anabolic/androgenic steroids (e.g. testosterone), glucocorticoids, appetite stimulants (e.g. dronabinol), cytokine modulators (e.g. thalidomide), angiotensin and beta-adrenoreceptor inhibitors, NHE-1 inhibitors (e.g. rimeporide), antifibrotic drugs (e.g. losartan or Lisinopril), phosphodiesterase 5 (PDE5) inhibitors (e.g. tadalafil or sildenafil), dehydroepiandrosterone, Vitamin D, ursolic acid, omega 3 acids, angiotensin-converting enzyme (ACE) inhibitors, proteasome inhibitors, cyclophilin D inhibitors, PGC-1 a (alpha) pathway modulators, myostatin and activin A antagonists, ghrelin agonists, β2-adrenoreceptor agonists, creatine supplements, antifibrotic drugs such as losartan and lisinopril, muscle ischemia therapies such as tadalafil and sildenafil, mutation specific therapies such as exon skipping therapies (e.g. eteplirsen, a morpholino phosphorodiamidate antisense oligomer targeting mutations implicated in DMD cases), agents for therapeutic nonsense suppression such as ataluren, utrophin upregulators such as SMT-C1100, gene replacement therapies (such as using rAAV2.5-CMV-Mini-dystrophy, rAAVrh74.MCK.Mini-dystrophy or rAAV1.CMV.huFollistatin344) or cell therapies using muscle precursor cells or stem cells.

Such combination therapies noted above encompass combined administration (where two or more therapeutic agents are included in the same or separate formulations), and separate administration, in which case, administration of the LSD1 inhibitor can occur prior to, simultaneously, and/or following, administration of the additional therapeutic agent.

The LSD1 inhibitor (and any additional therapeutic agent) can be administered by any suitable means, including parenteral, oral, transmucosal or topical administration, preferably oral administration.

The doses used for the administration can be adapted as a function of various parameters, and in particular as a function of the mode of administration used, of the relevant pathology, or alternatively of the desired duration of treatment. The LSD1 inhibitor (and any additional therapeutic agent) may be administered as a single dose or in multiple doses.

The amount of LSD1 inhibitor which will be effective in the treatment of a particular disorder or condition will depend on the nature of the disorder or condition, and can be determined by standard clinical techniques.

In a preferred embodiment, each dose may range from about 0.05 mg to about 250 mg per kilogram of body weight of compound of LSD1 inhibitor, preferably from about 0.1 mg to about 200 mg per kilogram of body weight, and more preferably from about 1 mg to about 150 mg per kilogram of body weight of LSD1 inhibitor, and even more preferably from about 10 mg to about 120 mg per kilogram of body weight of LSD1 inhibitor.

The dosing schedule for administration may vary from once a month to daily depending on a number of clinical factors, including the type of disease, severity of disease, and the subject's sensitivity to the therapeutic agent.

As shown in the experimental section, the LSD1 inhibitors are able to prevent muscle atrophy.

The present invention thus also concerns a product containing a LSD1 inhibitor as described above and a compound inducing skeletal muscular atrophy, as a combined preparation for simultaneous, separate or sequential use.

All embodiments described above for the LSD1 inhibitors as skeletal muscle hypertrophy inducers are also encompassed in this aspect.

In a particular embodiment, the compound inducing skeletal muscular atrophy is a therapeutic agent. In this embodiment, the LSD1 inhibitor is used to prevent or limit drug-induced myopathy.

The present invention further concerns a method for preventing or limiting the skeletal muscular atrophy induced by a therapeutic agent in a subject comprising administering a therapeutically effective amount of a LSD1 inhibitor as described above to said subject simultaneously, separately or sequentially to the administration of said therapeutic agent inducing skeletal muscular atrophy.

Examples of therapeutic agents inducing skeletal muscular atrophy include, but are not limited to corticosteroids, colchicine, chloroquine, hydroxychloroquine, D-penicillamine, antibiotics, betablockers, amiodarone, cimetidine, zidovudine, vincristine, clofibrate, statins, fibrates, cyclosporine, L-tryptophan, drugs causing hypokalaemia and lipid lowering agents, or combinations of drugs such as a fibrate and a statine or cyclosporin and colchicine, and therapeutic agents administered by intramuscular route such as vaccines.

In a preferred embodiment, the therapeutic agent inducing skeletal muscular atrophy include is a lipid lowering agent, preferably selected from statins and fibrates.

The LSD1 inhibitor and the therapeutic agent inducing skeletal muscular atrophy may be administered simultaneously. Alternatively, the LSD1 inhibitor may be administered to the subject prior or after administration of the therapeutic agent inducing skeletal muscular atrophy. Preferably, when the therapeutic agent and the LSD1 inhibitor are administered separately, they are both administered within 24 hours.

LSD1 inhibitors as described above, i.e. skeletal muscle hypertrophy inducers, may also find applications in feed and food industries, in particular as dietary supplements.

Accordingly, in a further aspect, the present invention also relates to a dietary supplement composition comprising a LSD1 inhibitor.

It also relates to a non-therapeutic use of a LSD1 inhibitor as defined above, or of a dietary supplement composition of the invention to increase muscle mass, muscle strength and/or muscle performance in a subject.

It further relates to a non-therapeutic use of a LSD1 inhibitor as defined above, or of a dietary supplement composition of the invention for use to prevent loss of skeletal muscle mass, preferably involuntary and/or undesired loss of skeletal muscle mass.

The subject is preferably a mammal, more preferably a human being.

In an embodiment, the subject is a non-human animal, preferably a mammal, and even more preferably a livestock animal or a sports or leisure animal, e.g. racehorses. Livestock animals are non-human mammals, preferably mammals used for meat. In particular livestock animals may be selected from pig, cattle, goat, sheep, horse, bison, deer, elk or moose.

In another embodiment, the subject is a human being, preferably an adult human.

In a particular embodiment, the subject is an older adult human, e.g. of more than 60, and the dietary supplement composition is used, or is suitable, to stop, slow/down or prevent muscle function and/or mass decline.

The subject is preferably a healthy subject, i.e. a subject who is not suffering from a disease or disorder resulting in loss of skeletal muscle tissue and/or muscle weakness.

The dietary supplement composition may be in the form of a powder, liquid, or solid.

Preferably, the dietary supplement composition is formulated for oral administration. In particular, said dietary supplement composition may be formulated into conventional oral dosage forms such as tablets, capsules, powders, granules and liquid preparations such as syrups, elixirs, and concentrated drops. Non toxic solid carriers or diluents may be used which include, for example, mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and cross-linked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

The dietary supplement composition may comprise further ingredient providing beneficial effects to the subject such as vitamins (e.g. vitamin D), amino acids, proteins, lipids (omega 3 fatty acids), ursolic acid, tomaditine, antioxidants, polyphenols, isoflavones present in soybean and derivatives, tea leaves components and garlic compounds.

All embodiments described above for the LSD1 inhibitors and their uses, in particular, as skeletal muscle hypertrophy inducers are also encompassed in this aspect.

The present invention also relates to the use of a LSD1 inhibitor as defined above, as ingredient for animal feed composition or as additive for animal feed composition. It also relates to the use of a LSD1 inhibitor, to prepare an ingredient or additive for animal feed composition. It further relates to an ingredient or additive for animal feed composition comprising a LSD1 inhibitor as defined above.

It further relates to a feed composition for livestock comprising a LSD1 inhibitor as defined above, as ingredient or additive.

The feed composition, ingredient, additive, or dietary supplement of the invention may further comprise any edible GRAS (generally recognized as safe) material such as, for example, corn gluten feed, sunflower hulls, distillers grains, guar hulls, wheat middlings, rice hulls, rice bran, oilseed meals, dried blood meal, animal by-product meal, fish by-product, fish meal, dried fish solubles, feather meal, poultry by-products, meat meal, bone meal, dried whey, soy protein concentrate, soy flour, yeast, wheat, oats, grain sorghums, corn feed meal, rye, corn, barley, aspirated grain fractions, brewers dried grains, corn flour, corn gluten meal, feeding oat meal, sorghum grain flour, wheat mill run, wheat red dog, hominy feed, wheat flour, wheat bran, wheat germ meal, oat groats, rye middlings, cotyledon fiber, ground grains, or a mixture thereof.

Preferably, the feed composition, ingredient, additive, or dietary supplement of the invention is used as non-therapeutic skeletal muscle hypertrophy inducer, and in particular to improve livestock performance, i.e. to increase liveweight gain. Thus, preferably, the feed composition, ingredient, additive, or dietary supplement is intended to be administered to a healthy subject, i.e. a subject who is not suffering from a disease or disorder resulting in loss of skeletal muscle tissue and/or muscle weakness. The subject may be as defined above for the dietary supplement composition of the invention.

The invention also relates to a method of improving livestock performance and/or health comprising providing to said livestock a LSD1 inhibitor as defined above, in particular a feed composition, ingredient, additive, or dietary supplement of the invention. Preferably, as used herein, the term "improving livestock performance" refers to increase liveweight gain. This use is intended to be a non-therapeutic use as explained above and preferably, the compound, feed composition, ingredient, additive, or dietary supplement is intended to be administered to healthy livestock, i.e. who is not suffering from a disease or disorder resulting in loss of skeletal muscle tissue and/or muscle weakness.

The feed composition, ingredient, additive, or dietary supplement may be in the form of a powder, liquid, or solid.

Ingredients of the feed composition of the invention other than the LSD1 inhibitor depend on the nature of the livestock and may be easily chosen by the skilled person.

Preferably, the feed composition of the invention is in a form and/or a composition approved by a governmental institution such as National Food Administration (for example ANSES in France, ACIA in Canada, or FAD in the US).

All embodiments described above for the LSD1 inhibitors and its uses, in particular, as skeletal muscle hypertrophy inducers are also encompassed in this aspect.

The following examples are given for purposes of illustration and not by way of limitation.

EXAMPLES

Example 1

Materials and Methods
Cell Source and Cell Culture

Healthy donor primary skeletal cells (Donor 1 and Donor 3) were Clonetics™ Human Skeletal Muscle Myoblasts (HSMM).

Donor characteristics are detailed in table 1 below.

TABLE 1

| Donor characteristics | | |
| --- | --- | --- |
|  | Donor1 | Donor 3 |
| Source | Lonza | Lonza |
| Donor Age | 16 years | Male |
| Donor Sex | Female | 21 years |
| Donor Race | Caucasian | Caucasian |
| Status | Healthy | Healthy |
| Desmin positive cells | >90% | >90% |

Muscle cells were maintained in culture following the supplier instructions with supplements and fetal bovine serum (FBS) serum provided by Lonza. An amplification step was performed in order to obtain enough cells for seeding the screening plates.

Hypertrophy Assay and Atrophy Rescue Assays

Hypertrophy and Atrophy Rescue assays were performed using an in vitro fully automated human myotube model called MyoScreen™ (Cytoo, France). This model relies on a tight control of the microenvironment that guides the differentiation of human primary myoblasts. Myotubes formed on MyoScreen™ micropatterns present a high level of maturation together with a highly standardized morphology.

Human primary myoblasts from donors were seeded in MyoScreen™ micropatterned 96-well plates (Cytoo, France), let them adhere for 24 h in growth medium, then run the differentiation in a low horse serum medium for at least 5 days.

At Day 0, MyoScreen™ plates (Cytoo, France) containing micropatterns were pre-filled with 200 µl/well of growth medium and stored in the incubator at 37° C. Human primary myoblasts were detached from the flasks, count, and seeded into the plates with 15 000 cells per well in 100 µl of growth medium.

At Day 1, the growth medium was changed for a differentiation medium, 300 µ/well (DMEM with 0.1% horse serum) in which myoblasts started differentiating and forming myotubes.

At Day 2, the differentiation medium was changed. Then candidate compounds were diluted with differentiation medium and transferred into the plate. The final concentration of DMSO should be not higher than 0.1%. At least 6 wells were treated with the vehicle as a basal control, and 6 wells were treated with IGF-1 at 100 ng/ml as positive hypertrophy control.

For Atrophy Rescue assay, one hour after candidate compound addition, atrophy inducers were added at the following final concentration: 150 ng/mL of myostatin, 25 ng/mL of IL-1β, 2 ng/mL of TNF-α, 0.5 ng/mL of TGF-β and 100 µM of dexamethasone.

At Day 6, cells were fixed with formalin 5% for 30 min at room temperature, then permeabilized with Triton X-100 at 0.1% in PBS for 15 min, and blocked with PBS+BSA 1% for 20 minutes. Myotubes were incubated with first antibody against Troponin T in blocking buffer for 1 h30, washed three times with PBS, incubated with secondary antibody and Hoescht (1/10000) for 1 h30, and washed three times with PBS.

Image Analysis

Images were acquired at 10× magnification with an Operetta High Content Imaging System. Image processing and analysis were performed with dedicated algorithms developed on the Acapella High Content Imaging Software (Perkin Elmer) by CYTOO. Eleven fields per well were acquired.

First, segmentation of myotubes and nuclei were done using respectively the Troponin T staining intensity and the Hoechst staining. One to two myotubes per micropattern were usually identified (a myotube is a troponin T staining area that includes at least 2 nuclei). The threshold of segmentation was set-up in order to avoid detecting the background noise and eliminate aberrant small myotube structures. At the end of this first step, specific readouts were calculated in the whole well, like the nuclei count and the fusion index (percentage of nuclei included in troponin T staining) Usually around 50 to 60 myotubes were detected per well in a control condition.

Then, an image clean-up step was performed on the Troponin T images in order to remove myotubes that touch the border of the image. The final valid myotubes were used to extract myotube morphology parameters including the myotube width and area, and the number of nuclei per myotube.

Nuclei Count, Fusion Index, Mean myotube Area and Number of nuclei per myotube have been validated as relevant and sensitive readouts of myotube differentiation as well as atrophic and hypertrophic induction.

Primary Screening

A primary screening was run to identify hypertrophy compounds that increase the myotube differentiation and size. Candidate compounds were tested at 10 µM in monoplicate on Donor 3 cells.

Retest

A retest was run, by cherry picking (same compound batch as primary screening): each hit was tested in the same conditions as in the Primary Screening (Donor 3, 10 µM) in six well replicates.

Dose Response on Two Healthy Donors

Dose response assays were performed on two healthy donors (Donors 3 and 1): 8 doses of candidate compounds between 33 µM and 0.015 µM, 2 well replicates per dose.

$EC_{50}$ Calculation

Compounds of interest were tested several times in dose response, with triplicate of wells per dose. Results were normalized to the control condition (basal level), and plotted using GraphPad Prism. The readout "nuclei count" allowed detecting any toxicity effect. The readouts "fusion index" and "myosin area" were used to determine the $EC_{50}$ value using the GraphPad Prism fitting solution.

Atrophy Rescue Evaluation

Atrophy Rescue assays were performed in triplicate in the presence of atrophy inducers, i.e. TNF-α, IL-1β, Myostatin, TGF-β and dexamethasone, and at 1 µM tranylcypromine.

Results

As shown on Table 2 below, tranylcypromine was identified as skeletal muscle hypertrophy inducers during the primary screening and the retest, inducing an increase in the fusion index or/and myotube area readouts by more than +30%.

TABLE 2

Hypertrophy activity on the healthy donor 3

| Compounds | Primary screening (% Activity) | Retest (% Activity) |
| --- | --- | --- |
| tranylcypromine | 176 | 136 |
| IGF-1 (positive control) | 210 | 190 |

(%) Activity = Myotube fusion index (compound) *100/Myotube Fusion index (basal control)

Dose responses were performed on two healthy donors. Results are presented in Table 3. Tranylcypromine was active on both healthy male and female donors. its $EC_{50}$ could not be defined precisely because the dose response range was too high to detect both minimum and maximum activity levels.

TABLE 3

Results of the first dose response assay on two different donors

| Compounds | Donor 3 | | Donor 1 | |
| --- | --- | --- | --- | --- |
| | % Activity | $EC_{50}$ | % Activity | $EC_{50}$ |
| Tranylcypromine | 127 | <30 nM | 138 | <300 nM |
| IGF-1 | 150 | | 150 | |

In order to determine the $EC_{50}$ more precisely, a second dose response was run on the healthy donor 3, testing lower concentrations. Furthermore two additional LSD1 inhibitors were tested, namely RN 1 dihydrochloride and GSK LSD1. Results are shown in Table 4. $EC_{50}$ value below the micromolar range was confirmed.

TABLE 4

Results of the second dose response assay on the healthy donor 3

| | Donor 3 | |
| --- | --- | --- |
| Compounds | % Activity | $EC_{50}$ |
| Tranylcypromine | 135 | 50 nM |
| RN 1 dihydrochloride | 135 | 100 pM |
| GSK LSD1 | 145 | 100 pM |
| IGF-1 | 150 | |

Atrophy rescue assays was performed for tranylcypromine. Myotubes from the healthy donor 3 were atrophied using different inducers: TNF-α, IL-1β, Myostatin, TGF-β and dexamethasone. The ability of tranylcypromine to block the atrophy induced by these different atrophy inducers was determined.

Results presented in Table 5 demonstrate that tranylcypromine can inhibit the atrophy induced by IL-1β, TNF-α, Myostatin, TGF-β and dexamethasone.

TABLE 5

Results of atrophy rescue assays

| Compounds | IL-1 | TNF-alpha | Myostatin | TGF-β | dexa-methasone |
|---|---|---|---|---|---|
| Tranylcypromine | +++ | + | +++ | + | ++ |
| IGF-1 | +++ | +++ | +++ | ++ | +++ |

(+++: total rescue, ++: partial rescue, + low rescue)

Example 2

Dose response assays were performed with GSK LSD1 and Bizine on five healthy donors Donor characteristics are detailed in table 6 below.

TABLE 6

Donor characteristics

| | Donor 3 | Donor 5 | Donor 7 | Donor C1 | Donor C13 |
|---|---|---|---|---|---|
| Source | Lonza | Lonza | Lonza | Hospital | Hospital |
| Donor age (years) | 21 | 20 | 37 | 1 | 13 |
| Donor sex | Male | Female | Male | Male | Male |
| Donor race | Caucasian | Caucasian | Caucasian | Caucasian | Caucasian |
| Status | Healthy | Healthy | Healthy | Healthy | Healthy |
| Desmin positive cells | >90% | >90% | >90% | >90% | >90% |

The assays were performed as described in example 1 and results are shown in Table 7.

TABLE 7

Results of the dose response assays on the healthy donors 3, 5, 7, C1 and C13

| | Donor 3 | | Donor 5 | | Donor 7 |
|---|---|---|---|---|---|
| Compounds | % Activity | $EC_{50}$ | % Activity | $EC_{50}$ | % Activity |
| Bizine | 120 | <350 nM | 119 | 87 nM | 116% at 1 μM |
| GSK LSD1 | | | 146 | 12 pM | 120% at 1 μM |
| IGF-1 | 190 | | 145 | | 119 |

| Compounds | Donor C1 % Activity | Donor C13 % Activity |
|---|---|---|
| GSK LSD1 | 154% at 1 μM | 123% at 1 μM |
| IGF-1 | 124 | 141 |

Example 3—In Vivo Assay

The benefits of GSK-LSD1 on skeletal muscle function of a mouse model of Duchenne muscular dystrophy, the DMD mdx mouse, is evaluated.

After 6 weeks of treatment at 10 mg/day/kg an analysis of muscle function is performed 1) in vivo, by carrying out the grip test and wire test, 2) in situ by the analysis of contractile properties of isolated muscle and 3) in vitro, by analyzing the contractile properties of isolated permeabilized fibers from the diaphragm, a muscle described as one of the most affected muscles in the DMDmdx mouse. These approaches are completed by an analysis of plasma creatine kinase levels (CK), an indicator of muscle injury.

Example 4

Figure 1B:
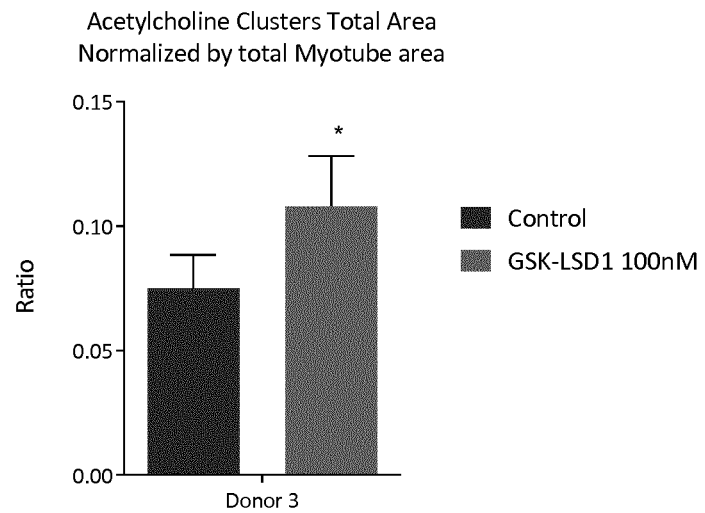

Material and Method
Acetylcholine Receptor (AchR) Clustering Assay
The MyoScreen™ protocol was performed as described in the Hypertrophy and Atrophy rescue assay in example 1 but was stopped at Day 9 instead of Day 6. At the end of the assay, AchR were immunostained using a specific antibody in addition to Troponin T and nuclei. Images were acquired at ×20 with an Operetta High Content Imaging System from Perkin Elmer. Image processing and analyses were performed with a dedicated algorithm developed on the Acapella High Content Imaging Software (Perkin Elmer). Specific readouts were calculated in each well: nuclei count and myotube fusion index, number of AchR, AchR mean area, AchR total area normalized by the myotube total area.
Results
Remarkably, when labeled with a specific anti-AChR antibody, MyoScreen myotubes at 6 days post-differentiation display AChR clusters punctuated along the sarcolemma membrane in the middle of the myotube fiber and in distinct regions at the ends of myotubes. To develop an automated AChR cluster assay, an AChR detection routine was developed that was sensitive and robust enough to analyze aggregate number and size clusters in images using the Operetta/Acapella system (see Materials and Methods). The effect of GSK-LSD1 on AchR clustering was evaluated to demonstrate the compound positive effect on neuromuscular junction using two healthy donors (Donor 3 and Donor5). After 7 days of treatment, GSK-LSD1 increases significantly the AchR cluster total area by +260% in the Donor 5 model, and by +50% in Donor 3 (cf. FIG. 1).

The invention claimed is:

1. A method of treating a disease or disorder resulting in loss of skeletal muscle tissue and/or muscle weakness comprising the administration of an LSD1 inhibitor to a patient having said disease or disorder, wherein the LSD1 inhibitor is selected from the group consisting of RN-1, GSK LSD1 and bizine, and any pharmaceutically acceptable salt, hydrate, solvate or prodrug thereof.

2. The method according to claim 1, wherein said LSD1 inhibitor is GSK LSD1, or any pharmaceutically acceptable salt, hydrate, solvate or prodrug thereof.

3. The method according to claim 1, said method causing skeletal muscle hypertrophy and/or skeletal muscle regeneration and/or reducing skeletal muscle atrophy.

4. The method according to claim 1, wherein the disease or disorder resulting in loss of skeletal muscle tissue and/or muscle weakness, is selected from sarcopenia, cachexia, neuromuscular diseases, a muscular dystrophy, muscle disuse atrophy, atrophy induced by anorexia food starvation, muscle injuries, acute muscular injury or muscle overuse injury.

5. The method according to claim 1, wherein the disease or disorder resulting in loss of skeletal muscle tissue and/or muscle weakness is sarcopenia, cachexia, a neuromuscular disease or a muscular dystrophy.

6. The method according to claim 4, wherein the muscular dystrophy is selected from the group consisting of Duchenne muscular dystrophy, Becker muscular dystrophy, myotonic muscular dystrophies, distal muscular dystrophies, Miyoshi muscular dystrophy, and limb-girdle muscular dystrophies.

7. The method according to claim 1, wherein the disease or disorder resulting in loss of skeletal muscle tissue and/or muscle weakness, is selected from muscle disuse atrophy, atrophy induced by anorexia food starvation, and muscle injuries including acute muscular injury or muscle overuse injury.

8. A method to increase muscle mass, muscle strength and/or muscle performance in a subject comprising the administration of an LSD1 inhibitor to said subject, wherein the LSD1 inhibitor is selected from the group consisting of RN-1, GSK LSD1 and bizine, and any pharmaceutically acceptable salt, hydrate, solvate or prodrug thereof.

9. A method of reducing loss of skeletal muscle mass in a subject comprising the administration of an LSD1 inhibitor to said subject, wherein the LSD1 inhibitor is selected from the group consisting of RN-1, GSK LSD1 and bizine, and any pharmaceutically acceptable salt, hydrate, solvate or prodrug thereof.

* * * * *

UNITED STATES PATENT AND TRADEMARK OFFICE
CERTIFICATE OF CORRECTION

PATENT NO. : 11,382,872 B2
APPLICATION NO. : 16/461076
DATED : July 12, 2022
INVENTOR(S) : Pauline Poydenot et al.

Page 1 of 1

It is certified that error appears in the above-identified patent and that said Letters Patent is hereby corrected as shown below:

In the Specification

<u>Column 24,</u>
Line 53, "300 μ/well" should read --300 μl/well--.

Signed and Sealed this
Fourth Day of April, 2023

Katherine Kelly Vidal
*Director of the United States Patent and Trademark Office*